United States Patent
Wong et al.

(10) Patent No.: US 6,518,428 B1
(45) Date of Patent: *Feb. 11, 2003

(54) PROCESS FOR PREPARING AMINE PLATINUM COMPLEXES

(75) Inventors: Ernest S. Y. Wong, Langley (CA); Christen M. Gianomenico, Blaine, WA (US)

(73) Assignee: Anormed, Inc., Langley B.C. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/547,074

(22) Filed: Apr. 11, 2000

Related U.S. Application Data (60) Provisional application No. 60/128,939, filed on Apr. 13, 1999.

(51) Int. Cl.$^7$ .................. C07D 213/02; C07F 15/00; A61K 31/282; A61P 35/00
(52) U.S. Cl. ............. 546/2; 546/8; 546/9; 546/10; 544/4; 556/136; 556/137; 514/184; 514/188
(58) Field of Search .................. 556/136, 137; 514/492, 184, 188; 546/8, 9, 2, 10; 544/4

(56) References Cited

U.S. PATENT DOCUMENTS

| | | | |
|---|---|---|---|
| 4,329,299 A | 5/1982 | Hydes | |
| 4,533,502 A | 8/1985 | Rochon et al. | |
| 4,760,155 A | * 7/1988 | Heffernan | 556/136 |
| 5,194,645 A | 3/1993 | Barnard | 556/137 |
| 5,244,919 A | 9/1993 | Abrams et al. | 514/492 |
| 5,547,982 A | 8/1996 | Abrams et al. | 514/492 |
| 5,665,771 A | * 9/1997 | Murrer | 514/492 |

FOREIGN PATENT DOCUMENTS

| | | |
|---|---|---|
| GB | 2137198 A | 10/1984 |
| WO | WO 00/56743 | 9/2000 |
| WO | WO 00/61590 | 10/2000 |

OTHER PUBLICATIONS

Kong PC and Rochon FD. Canadian J. Chem. (1976) 56, pp. 441–445.*
Giandomenico et al. Inorg. Chem. (1995) 34, pp. 1015–1021.*
Kong, P.–C. et al. (1978). "Reactions of Potassium Tetrachloroplatinate (11) with Pyridine Derivatives in Dimethylformamide and Synthesis of Potassium Trichloro(pyridine)platinum(11)," *Chemical Abstracts* 89(4):abstract No.35686.
Rochon, F.D. et al. (1988). "Synthesis and Studies of Platinum (11) Compounds of the Types K'Pt(amine)C13! and Pt(amine)(acetonitrile)C12!," *Chemical Abstracts* 108(24):abstract No.215224.
Talman, E. G. et al. (1997). "Crystal and Molecular Structures of Asymmetric cis– and trans–Platinum(11/1V) Compounds and Their Reactions with DNA Fragments," *Chemical Abstracts* 126(4): abstract No.194433.

Abrams et al., Inorg. chim. Acta (1987) 131:3–4.
Holford et al., Anti–Cancer Drug Des. (1998) 13:1.
Holford et al., Br. J. Cancer (1998) 77:366.
Kelland et al., Cancer Res. (1992) 52:822.
Kelland et al., Cancer Res. (1992) 52:3857.
Kelland et al., Cancer Res. (1993) 53:2581.
Raynaud et al., Clin. Cancer Res. (1997) 3:2063–2074.
Wong et al., Chem. Rev. (1999) 9:2451–2466.
Braddock, P.D. et al., Chem.–Biol. Interactions, 11:145–161 (1975).
Courtot, P. et al., J. Organometallic Chem., 145:343–357 (1978).
Giandomenico, C.M. et al., Inorg. Chem., 34:1015–1021 (1995).
Kong, P.–C. et al., Can J. Chem., 57:682–684 (1979).
Rochon, F.D. et al., Can J. Chem., 64:1894–1896 (1986).
Rochon, F.D. et al, Can J. Chem., 56:441–445 (1978).
Rochon, F.D. et al., Can J. Chem., 74:2121–2130 (1996).
Rochon, F.D. et al., Can J. Chem., 58: 97–101 (1980).
Rochon, F.D. et al., Can J. Chem., 33:4485–4493 (1994).

* cited by examiner

*Primary Examiner*—Evelyn Mei Huang
(74) *Attorney, Agent, or Firm*—Morrison & Foerster LLP (57) ABSTRACT

The present invention relates to the area of platinum drugs. In particular, it relates to an improved process for preparing platinum complexes having the general formula (Ia) or (Ib): as defined of herein,

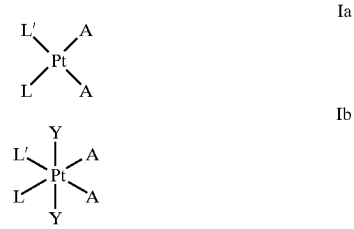

comprising:
1a) a first step, wherein $[PtA_4]^{2-}$ is reacted with L under appropriate conditions in a first solvent to form $[PtA_3(L)]^-$;

1b) a second step, wherein $[PtA_3(L)]^-$ is reacted with L' under appropriate conditions in a second solvent to form cis-$[PtA_2(L')(L)]$;

1c) in the case where Y is halogen or hydroxy a third step, wherein cis-$[PtA_2(L')(L)]$ is reacted with $H_2O_2$, $Y_2$ or halogen containing oxidant to form c,t,c-$[PtA_2Y_2(L')(L)]$; in the case where Y is carboxylate, carbamate or carbonate ester a fourth step, wherein an intermediate, where Y is hydroxy formed in step 1c), is functionalized with an appropriate acylating agent; and 1d) in the case where A is not a halide or is different from the original halide, additional step(s) in which the original halide A of an intermediate formed in step 1a or 1b 1c or 1d is converted to a different halide or a new leaving group(s) A such as mono-dentate hydroxy, alkoxy, carboxylate or bi-dentate carboxylate, phosphonocarboxylate, diphosphonate, or sulphate.

33 Claims, 5 Drawing Sheets

PROCESS FOR PREPARING AMINE PLATINUM COMPLEXES

This application claims the benefit of provisional application No. 60/128,939, filed on Apr. 13, 1999.

TECHNICAL FIELD

The present invention relates to the area of platinum drugs. In particular, it relates to an improved process for preparing platinum complexes having the general formula (Ia) or (Ib):

wherein:
- L and L' may be the same or different, provided that L' may be $NH_3$, but L may not be $NH_3$; and
- L and L' are each an amine or substituted amine that coordinates to the Pt atom through a nitrogen atom and is a heterocyclic amine or heteroaromatic amine or is represented by NRR'R", wherein R, R', or R" are independently selected from the group consisting of: hydrogen, substituted or unsubstituted straight, branched or cyclic aliphatic, aryl, nonaromatic or aromatic heterocyclic groups; and
  preferably L is a substituted amine wherein the substituent sterically hinders access of the Pt atom to a DNA strand of cell, preferably a tumor cell; and
- A may be the same or different and is a halogen or a leaving group such as hydroxy, alkoxide, carboxylate and may be the same or different or form a bi-dentate carboxylate, phosphoncarboxylate, diphosphonate or sulfate; and
- Y is a halogen, hydroxy, carboxylate, carbamate or carbonate ester.

BACKGROUND

Figure 1:
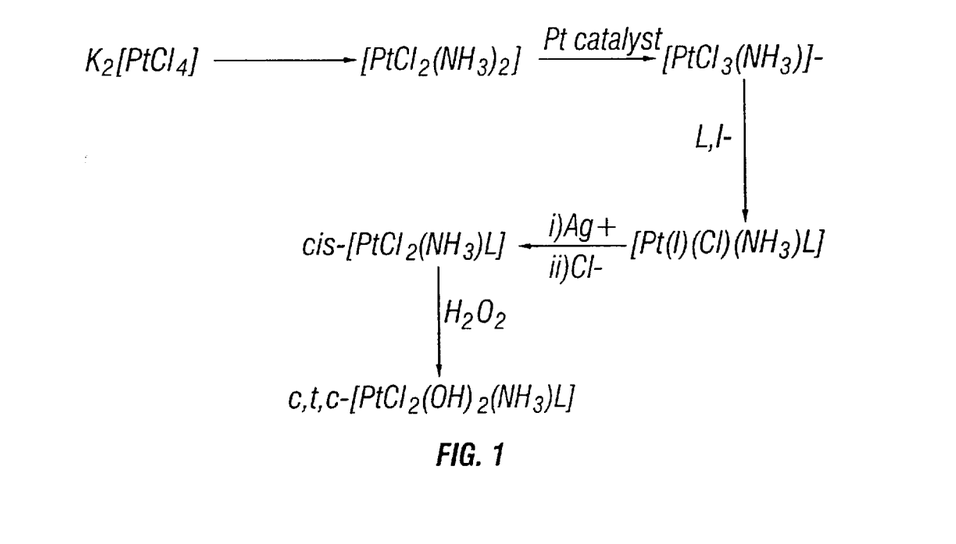
FIG. 1. Illustrates the synthesis of cis-$[PtCl_2(NH_3)(L)]$ and c,t,c$[PtX_2Y_2(NH_3)(L)]$ via $K[PtCl_3(NH_3)]$.

U.S. Pat. No. 4,329,299 and 5,665,771 describe platinum compounds and their usefulness as antitumor drugs. These two patents disclose platinum compounds that encompass complexes of the formula cis-[$PtA_2$(L')(L)] and c,t,c-[$PtA_2Y_2$(L')(L)], where A is a leaving group such as halogen, hydroxyl or carboxylate, L is an amine coordinated through the nitrogen atom and L' is an ammonium or substituted amine. The process for preparing these complexes disclosed in the patents are known in the art (Hydes, P. C. U.S. Pat. No. 4,329,299 (1982); Murrer, B. A. U.S. Pat. No. 5,665,771 (1997); Braddock, P. D.; Connors, T. A.; Jones, M.; Khokhar, A. R.; Melzack, D. H.; Tobe, M. L. *Chem.-Biol. Interactions* 1975, 11, 145–161; and Giandomenico, C. M.; Abrams, M. J.; Murrer, B. A.; Vollano, J. F.; Rheinheimer, M. I.; Wyer, S. B.; Bossard, G. E.; Higgins (III), J. D. *Inorg. Chem.* 1995, 34, 1015–1021). This process is illustrated in FIG. 1 with the synthesis of cis-[$PtCl_2(NH_3)$(L)] and c,t,c-[$PtCl_2(OH)_2(NH_3)$(L)] as examples. From the readily available and commonly used $K_2[PtCl_4]$ starting material, the synthesis of cis-[$PtCl_2(NH_3)$(L)] involves four steps and the synthesis of c,t,c-[$PtCl_2Y_2$($NH_3$)(L)] requires five steps. The synthesis of these complexes according to the process known in the art gives low overall yield. U.S. Pat. No. 4,329,299 discloses an overall yield from $K_2[PtCl_4]$ of less than 8%, while overall yields of 20–30% have been reported in U.S. Pat. No. 5,665,771 and in the literature (Khokhar et al. and Giandomenico et al.). The low overall yield is due to the many stages involved in the process and to the difficult and low yielding conversion of [$PtCl_2(NH_3)_2$] to [$PtCl_3(NH_3)$]$^-$, which requires the use of expensive Pt catalyst. The synthesis of K[$PtCl_3(NH_3)$] from [$PtCl_2(NH_3)_2$] is also not particularly robust and large scale synthesis producing K[$PtCl_3(NH_3)$] of consistent quality is difficult to achieve. The process described above further requires the use of silver and iodide ions, and generates silver and iodide contaminated waste products.

Figure 2:
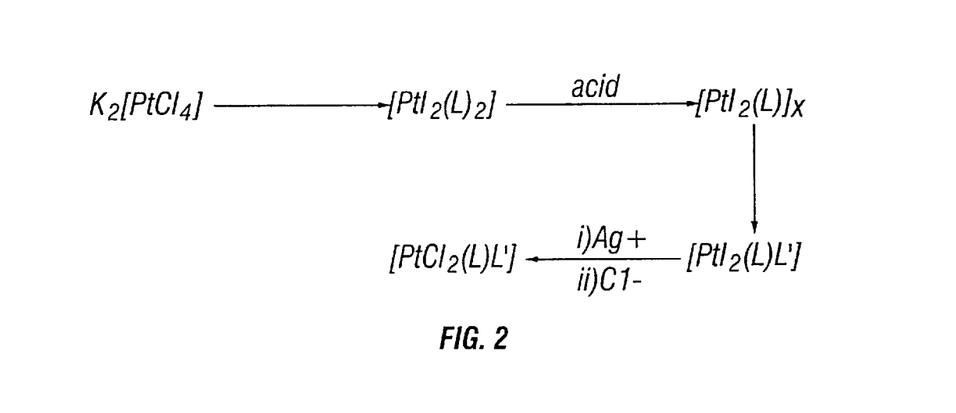
FIG. 2. Illustrates the synthesis of $[PtCl_2(L)L']$ via $[PtI_2(L)]_x$ oligomer.
Figure 3:
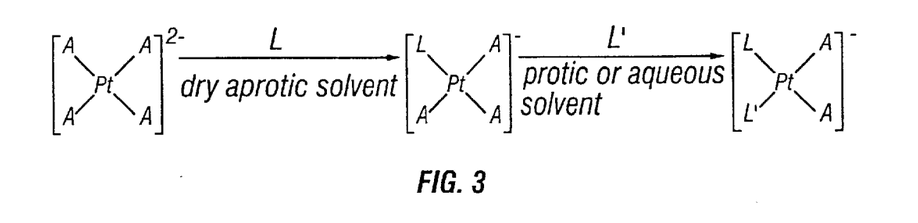
FIG. 3. Illustrates the synthesis of $[PtA_2(L')L]$ via the method of the present invention.

U.S. Pat. No. 4,533,502 and UK Patent GB 2137198A disclose a synthetic process to prepare [$PtX_2$(L)(L')] where L and L' are ligands bonded through amine nitrogen and L≠L' (Rochon, F. D.; Kong, P.-C. UK Patent GB2137198A (1984) and Rochon, F. D.; Kong, P.-C. U.S. Pat. No. 4,533,502 (1985)). The process is known in the art and the details of this synthetic process has been published (Courtot, P.; Rumin, R.; Peron, A.; Girault, J. P. J. *Organometallic Chem.* 1978, 145, 343–357 and Rochon, F. D.; Kong, P.-C. *Can. J. Chem.* 1986, 64, 1894–1896). FIG. 2 illustrates the process with [$PtCl_2$(L)(L')] as an example. From $K_2[PtCl_4]$, the process disclosed in U.S. Pat. No. 4,533,502 and UK Patent GB 2137198A involves 4 steps and the isolation of 3 intermediate products. The oligomer intermediate product is represented by [$PtLI_2$]$_x$ where x=2 to 4; multiple oligomer species are possible. The overall yield from $K_2[PtCl_4]$ was not disclosed in the patent. Silver and iodide ions are used in the process and corresponding silver and iodide contaminated wastes are generated.

[$PtCl_3L$]$^-$, where L is an amine other than $NH_3$, represent an intermediate in the present invention. The preparation of [$PtCl_3L$]$^-$ from a dilute solution of $K_2[PtCl_4]$ in dimethylformamide (DMF) where L are pyridine and pyridine derivatives has been reported (Rochon, F. D.; Kong, P.-C. *Can. J. Chem.* 1978, 56, 441–445 and Rochon, F. D.; Beauchamp, A. L.; Bensimon, C. *Can. J. Chem.* 1996, 74, 2121–2130). The preparation of [$PtCl_3L$]$^-$ in solvents other than DMF or $H_2O$, or with amine other than pyridine and pyridine derivatives have not been reported. The synthesis of K[$PtCl_3L$] in DMF as reported in the literature was performed at 65–80° C. and the yields of the isolated product ranged from 40% to 90% depending on the pyridine derivative. Synthesis of [$PtCl_3L$]$^-$ in DMF can produce reactive or unstable Pt DMF complexes that could interfere with subsequent reactions or decompose to give insoluble black Pt impurities. For example in *Can. J. Chem.* 1978, 56, 441, Rochon et al reported the precipitation of insoluble black material when K[$PtCl_3$(2,6-dimethylpyridine)] was dissolved in aqueous solution. It was also reported that an oily paste that contained [$PtCl_2$(DMF)(pyridine derivative)] and other impurities was obtained during the isolation of K[$PtCl_3$(4-methylpyridine)] and K[$PtCl_3$(pyridine)]. Examples of [$PtCl_2$(DMF)L] complexes have been reported (Kong, P.-C.; Rochon, F. D.; *Can. J. Chem.* 1979, 57, 682–684; Rochon, F. D.; Kong, P.-C.; Melanson, R. *Can. J. Chem.* 1980, 58, 97–101; and Rochon, F. D.; Melanson, R.; Doyon, M.; Butler, I. S. *Inorg. Chem.* 1994, 33, 4485–4493).

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein. Specifically, the present application claims benefit of priority to U.S. provisional patent application serial No. 60/128,939, which was filed on Apr. 13, 1999 and which provisional patent application is incorporated in its entirety by reference herein.

DISCLOSURE OF THE INVENTION

The present invention describes a more efficient and economical process for preparing Pt complexes of the form cis-[PtA$_2$(L')(L)] (formula Ia) and c,t,c-[PtA$_2$Y$_2$(L')(L)] (formula Ib) directly from inexpensive and readily available platinum starting material, preferably tetrahaloplatinite like [PtCl$_4$]$^{2-}$ or [PtBr$_4$]$^{2-}$.

wherein:

L and L' may be the same or different, provided that L' may be NH$_3$, but L may not be NH$_3$; and L and L' are each an amine or substituted amine that coordinates to the Pt atom through a nitrogen atom and is a heterocyclic amine or heteroaromatic amine or is represented by NRR'R", wherein R, R', or R" are independently selected from the group consisting of: hydrogen, substituted or unsubstituted straight, branched or cyclic aliphatic, aryl, nonaromatic or aromatic heterocyclic groups; and preferably L is a substituted amine wherein the substituent sterically hinders access of the Pt atom to a DNA strand of cell, preferably a tumor cell; and A may be the same or different and is a halogen or a leaving group such as hydroxy, alkoxide, carboxylatate and may be the same or different or form a bi-dentate carboxylate, phosphoncarboxylate, diphosphonate or sulfate; and Y is a halogen, hydroxy, carboxylate, carbamate or carbonate ester.

In one embodiment, the process of the present invention is preferred for preparation of compound of formula Ia.

Terms as used herein are based upon their art recognised meaning and from the present disclosure should be clearly understood by the ordinary skilled artisan. For sake of clarity, terms may also have particular meaning as would be clear from their use in context. For example, a ligand is an ion or molecule bound to and considered bonded to a metal atom or ion. Mono-dentate means having one position through which covalent or coordinate bonds with the metal may be formed. Bi-dentate means having two positions through which covalent or coordinate bonds with the metal may be formed. The present invention preferably is a mono-dentate coordination of the L and L' amine through the nitrogen atom to Pt. Further, "sterically hindered" is used according to common usage in the art. "Sterically hindered amine" therefore refers to an amine component that because of its size or bulk hinders or interferes with rotation or other function or property of any other component of the Pt complexes disclosed herein. The processes of the present invention are preferably used to prepare the compounds described in U.S. Pat. No. 5,665,771, (particularly the sterically hindered amines derived by formula Ia in '771 patent) which is incorporated in its entirety herein and specifically the definitions of substituent groups as disclosed therein are specifically incorporated by reference herein. By the term "substituted" what is meant herein, when in reference to both L and L' as a nitrogen-linked heterocyclic amine(s) or heteroaromatic amine(s), is that a substitute group is independently selected from the group consisting of: hydrogen, substituted or unsubstituted straight, branched or cyclic aliphatic, aryl, nonaromatic or aromatic heterocyclic groups; and preferably where L is a substituted amine, the substituent thereby sterically hinders access of the Pt atom to a DNA strand of cell, preferably a tumour cell. Examples of such substituted L or L', include, but are not limited to: alkyl amines which may include: methyl amine; dimethyl amine; tributyl amine; di-isopropyl amine; aryl amines which may include: aniline, toluidine, aminonaphthalene and aminoanthracene; heterocyclic amines which may include: piperidine, piperazine, and pyrrolidine; and heteroaromatic amines which may include: pyridine, pyrazoles, imidazoles, oxazoles, iso-oxazoles; pyrimidine, and pyrazine. Other substituents are available to the ordinary skilled artisan who would readily appreciate that such other substitutents may be employed in the present invention in a manner consistent with the present disclosure.

More specifically, for example, in the case of substituted cyclic amines, the substituent may be lower alkyl or alkoxy of 1 to 4 carbon atoms, (especially methyl or methoxy), halo, (especially chloro or bromo), or aryl, (especially benzyl). The substituent may itself be substituted by lower alkyl or halo. By the term "lower alkyl" is meant an alkyl group with from 1 to 6 carbon atoms. The cyclic amine may carry other substituents either adjacent to the coordinating nitrogen atom or elsewhere on the ring. Other substituents include electron-withdrawing or electron-donating substituents such as nitro and alkoxy eg methoxy. If the cyclic amine is a fused ring system where the fused ring is an aromatic ring in positions 2 and 3 of the cyclic amine, no other substituent is necessary, although a substituent may be present. It can also be envisioned that this invention may be used to make trans isomers. For the preferred embodiment, this invention is used to make the cis isomers.

To illustrate the invention, the synthesis of cis-[PtCl$_2$(NH$_3$)(L)] and c,t,c-[PtCl$_2$(OH)$_2$(NH$_3$)(L)] from [PtCl$_4$]$^{2-}$ are used as examples. The congeners cis-[PtBr$_2$(NH$_3$)(L)] and c,t,c-[PtBr$_2$(OH)$_2$(NH$_3$)(L)] can also be prepared in the same manner from [PtBr$_4$]$^{2-}$.

For the preparation of cis-[PtCl$_2$(NH$_3$)(L)], the improved process involves two steps with the first step being the conversion of a suspension or concentrated solution of [PtCl$_4$]$^{2-}$ to [PtCl$_3$L]$^-$ in aprotic solvents. The second step converts a suspension or concentrated solution of [PtCl$_3$L]$^-$ to cis-[PtCl$_2$(NH$_3$)(L)] in ammonium hydroxide solution. Compared to the synthetic processes currently used in the art, the improved process has fewer synthetic steps, fewer isolated products, requires smaller volumes of ecologically harmful solvents, generates less metal contaminated wastes and produces cis-[PtCl$_2$(NH$_3$)(L)] with higher overall yields. It also does not require the use of silver and iodide ions, and does not generate silver and iodide contaminated wastes. All steps in the process are robust, reproducible and consistently generate products of the same quality.

The first step of the improved process is the reaction of [PtCl$_4$]$^{2-}$ with the amine L under appropriate conditions in a first solvent to form [PtCl$_3$L]$^-$. The potassium salt of [PtCl$_4$]$^{2-}$, which is the most readily available, is commonly employed. However, other salts of [PtCl$_4$]$^{2-}$ could also be used. Appropriate conditions herein shall mean those reaction conditions that promote and facilitate the chemical reaction as disclosed and claimed. Specifically, the present invention provides that such appropriate conditions include, but are not limited to: temperature; pH; concentration of reactants; degree of agitation; mesh size of reactants; and other such conditions facilitating the disclosed chemical reactions. However, other appropriate conditions would be those familiar to the ordinary skilled artisan that result in the steps of the disclosed chemical reactions. To aid in the dissolution of $K_2[PtCl_4]$, it is preferred to use finely ground $K_2[PtCl_4]$ powder. It is preferred that $K_2[PtCl_4]$ be less than or equal to about 240 $\mu$M in size. It is more preferable to have $K_2[PtCl_4]$ be less than or equal to about 100 $\mu$M in size. In the reaction, 1 to 1.3 equivalents of the amine is reacted with 1 equivalent of $K_2[PtCl_4]$. More preferably, 1 to 1.2 equivalent of the amine is used. It is most preferred to have 1.05 to 1.15 equivalent of the amine react with 1 equivalent of $K_2[PtCl_4]$. Using high equivalents of the amine increase the rate of the reaction but could also increase the formation of side products and lower the yield of the reaction. Additionally, the amine, L, is added to the reaction mixture in small portions over a period of time. Preferably, the amine is added in two or more equal amounts or more preferably in 4 or more amounts.

The reaction can be performed at a temperature of about 30–100° C. but it is more preferred to perform the reaction at about 40–70° C. Most preferably, a temperature range of about 50–65° C. is used. In general, the higher the reaction temperature the greater the rate of the reaction between $[PtCl_4]^{2-}$ and the amine. However a high reaction temperature could increase the formation of side products or allow the formation of reactive and unstable Pt impurities. In solvents that are capable of coordinating to metal atoms like DMF, reaction temperature greater than or equal to about 60° C. may promote the formation of Pt solvent complexes, which would decompose or interfere with the next step of the process.

The reaction is performed in aprotic solvents. It is preferred that the solvent be anhydrous containing less than about 25% water but a water content of less than about 10% is preferred. Most preferably, a water content of less than about 3% is desired. The reaction can be performed in aprotic solvents such as acetone, chloroform, dichloromethane, dimethylacetamide, dimethylformamide and N-methylpyrrolidinone. N-methylpyrrolidinone is the most preferred solvent.

The first reaction step is performed at a ratio that is less than about (15 ml solvent)/(1 mmole platinum). A preferred embodiment of the present invention contemplates a ratio of solvent (ml) to Pt (mmol) that is about 3–6:1. However, in a more preferred embodiment of the present method, the first reaction step is performed at a solvent to Pt ratio of about 1–2:1.

Figure 4A:
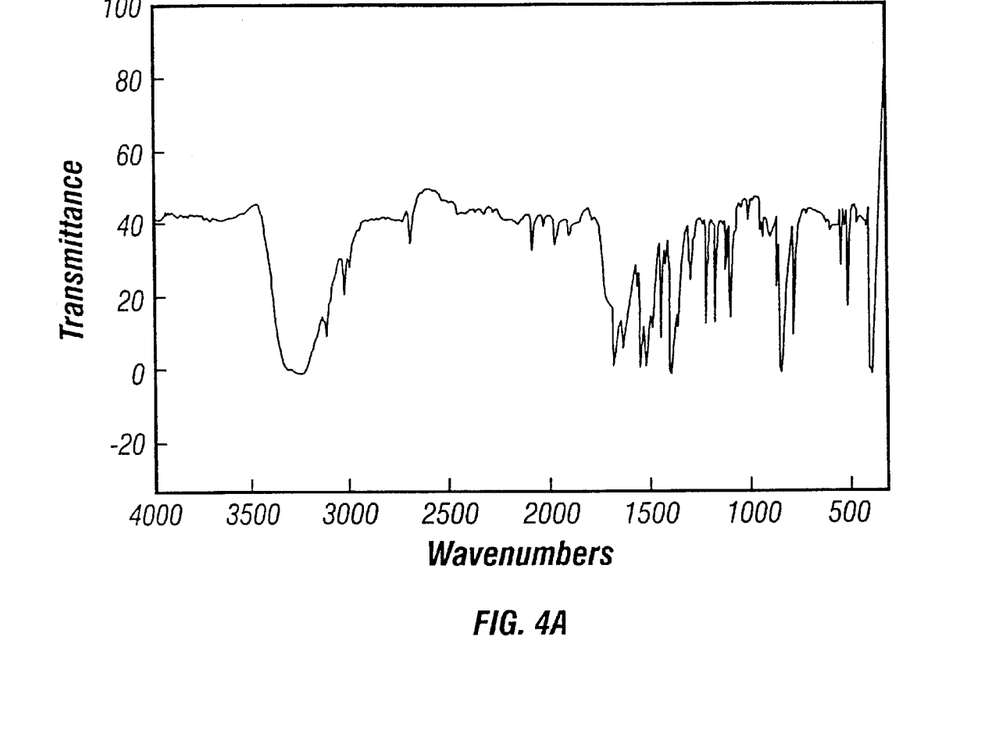
FIG. 4A. Infrared Spectrum of $[PtCl_2(NH_3)(2\text{-picoline})]$ prepared from the method disclosed in this invention.
Figure 4B:
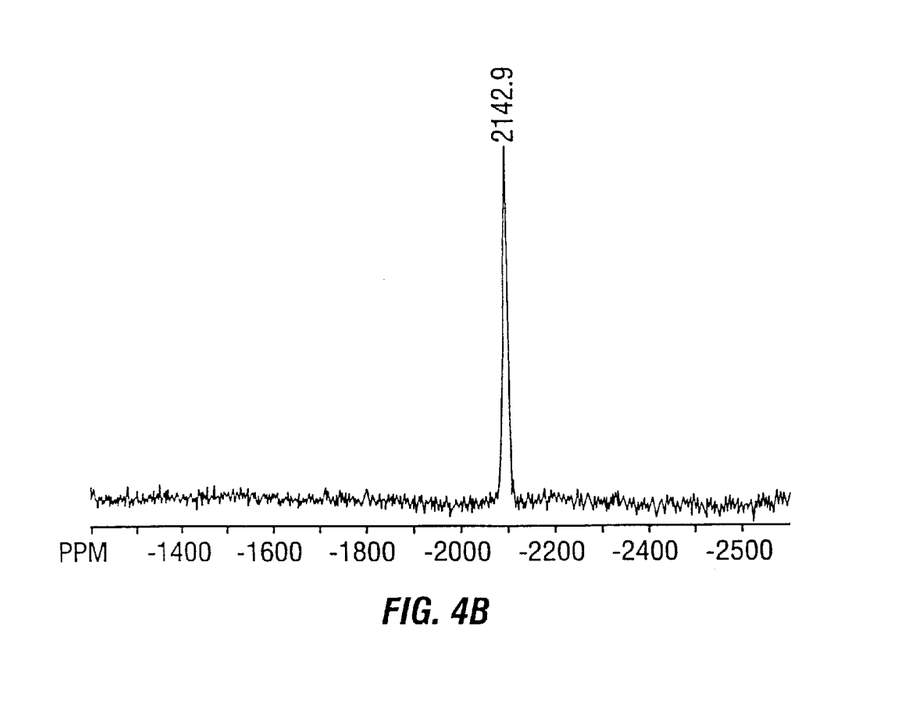
FIG. 4B. $^{195}Pt$ NMR Spectrum of $[PtCl_2(NH_3)(2\text{-picoline})]$ prepared from the method disclosed in this invention.
Figure 4C:
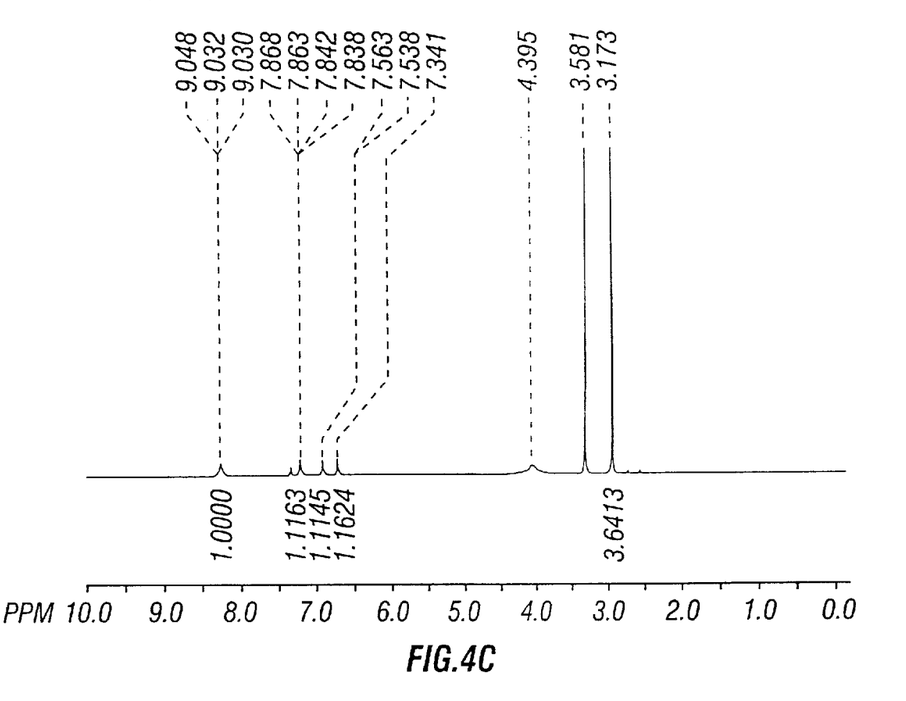
FIG. 4C. $^1H$ NMR Spectrum of $[PtCl_2(NH_3)(2\text{-picoline})]$ prepared from the method disclosed in this invention FIG. 5. Illustrates infrared and nuclear magnetic resonances spectrometric data for $[PtCl_2(NH_3)(2\text{-picoline})]$ prepared from the method known in the art as illustrated in FIG. 1.
Figure 5A:
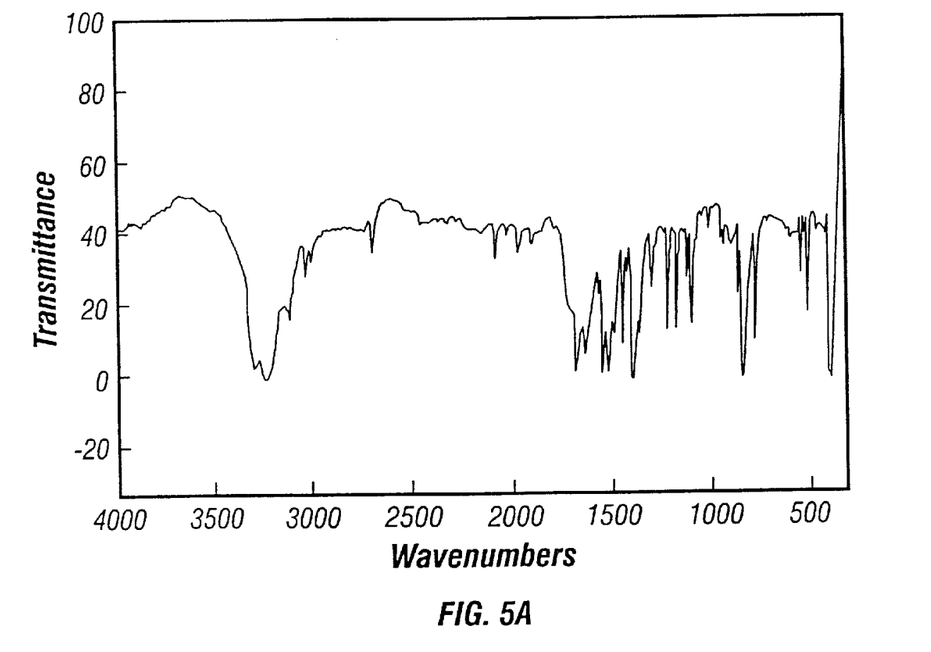
FIG. 5A. Infrared Spectrum of $[PtCl_2(NH_3)(2\text{-picoline})]$ prepared from the method known in the art as illustrated in FIG. 1.
Figure 5B:
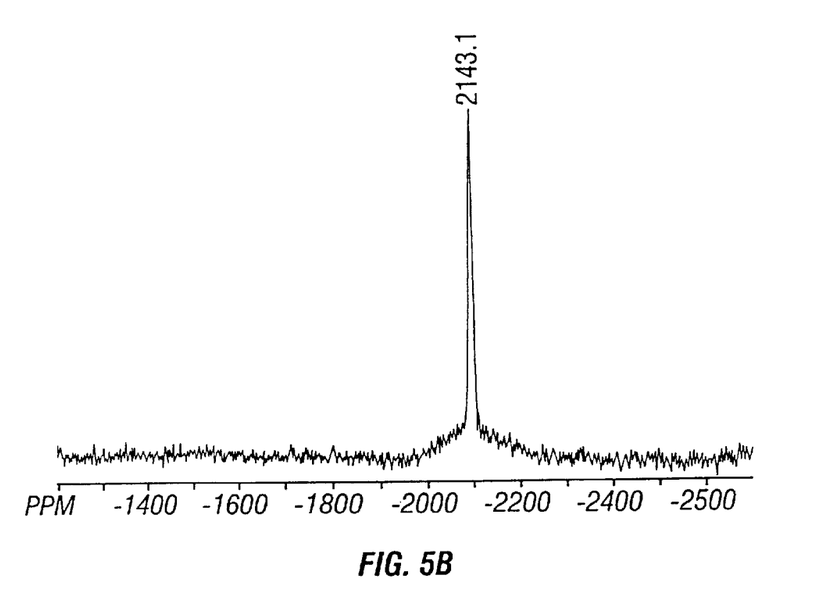
FIG. 5B. $^{195}Pt$ NMR Spectrum of $[PtCl_2(NH_3)(2\text{-picoline})]$ prepared from the method known in the art, as illustrated in FIG. 1.
Figure 5C:
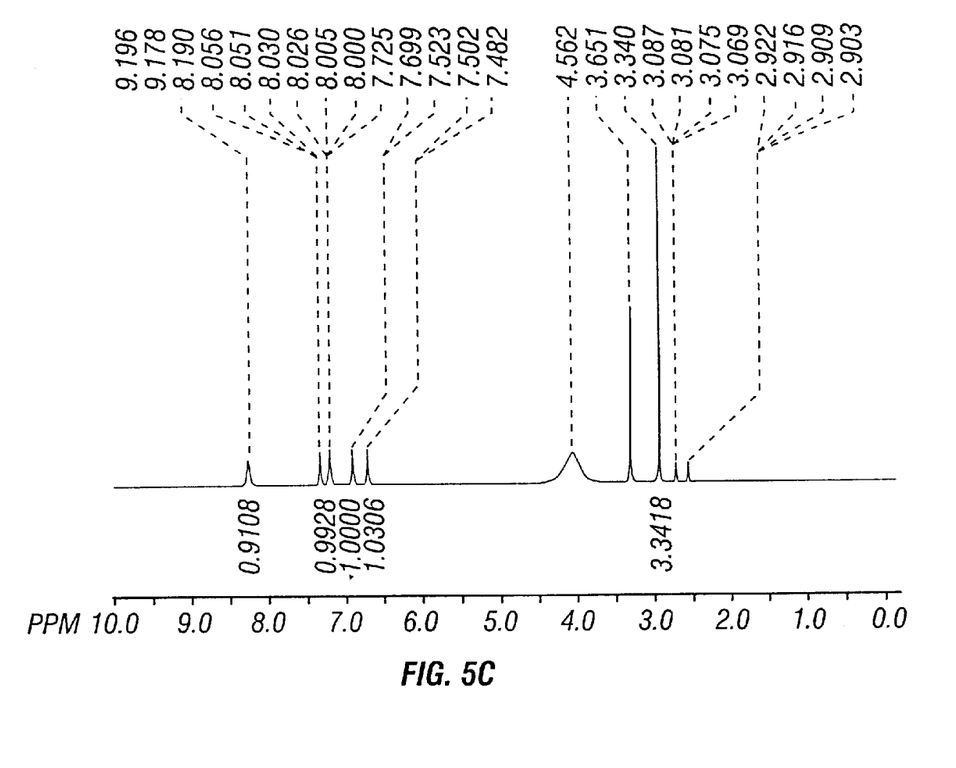
FIG. 5C. $^1H$ NMR Spectrum of $[PtCl_2(NH_3)(2\text{-picoline})]$ prepared from the method known in the art, as illustrated in FIG. 1.

The synthesis of $[PtCl_3L]^-$ in dimethylformamide (DMF), where L are pyridine or pyridine derivatives, are known in the literature (Rochon, F. D.; Kong, P.-C. Can. J. Chem. 1978, 56, 441–445; Rochon, F. D.; Beauchamp, A. L.; Bensimon, C. Can. J. Chem. 1996, 74, 2121–2130). For the synthesis of $K[PtCl_3(L)]$, $K[PtCl_3(2\text{-picoline})]$ is used as an illustrative example to compare the published method with the method disclosed in this invention. In the published method, the isolation of $K[PtCl_3(2\text{-picoline})]$ requires two separate steps during each of which solvents under reduced pressure are evaporated. In the evaporation of DMF under reduced pressure, heating at 40° C. is required. In large-scale industrial synthesis, the evaporation of solvents under reduced pressure, particularly with heating is a costly and time consuming procedure. In our preferred procedure, the synthesis and isolation of $K[PtCl_3(2\text{-picoline})]$ does not require the evaporation of solvents and does not require the transfer of the material from one solvent to another. The method disclosed in this invention is more efficient and is better suited for large-scale industrial production of the compound. The two methods produce $K[PtCl_3(2\text{-picoline})]$ in comparable yields and quality. Infrared and NMR spectroscopic data of $K[PtCl_3(2\text{-picoline})]$ produced using the method known in the art and with the method disclosed in this invention are shown on FIGS. 4 and 5. The synthesis of $[PtCl_3L]^-$ in other aprotic solvents such as acetone, chloroform, dichloromethane and N-methylpyrrolidinone was demonstrated in this invention.

The coordination of solvent molecules to Pt causing the formation of reactive or unstable Pt species poses a problem to the process described in this invention. In the published method (Rochon, F. D.; Kong, P.-C. Can. J. Chem. 1978, 56, 441–445), $[PtCl_2(DMF)(\text{pyridine derivative})]$ and other impurities were reported in the synthesis of $[PtCl_3(\text{pyridine derivative})]$. In this invention, we disclose a temperature range in which the formation of undesired species such as $[PtCl_2(DMF)(\text{pyridine derivative})]$ is minimized. The formation of black precipitate during the isolation of the product is indicative of the presence of reactive Pt impurities. Using the synthesis of $K[PtCl_3(2\text{-picoline})]$ in dimethylformamide as an example, no insoluble black precipitates are observed when the synthesis is performed below about 60° C. In our most preferred procedure, a reaction temperature of about 50–65° C. is used in the first reaction step. However, any temperature at which the formation of undesired species or reaction product impurities such as $[PtCl_2(DMF)(\text{pyridine derivative})]$ is minimized (<10%) or eliminated is contemplated by the present method.

Conversion of $[PtCl_3L]^-$ to $[PtCl_2(NH_3)L]$ in aqueous ammonia hydroxide is used to illustrate step 2 of the present invention. Step 2 is the reaction of a suspension or concentrated solution of $[PtCl_3L]^-$ with $NH_3$ in a second solvent to produce $[PtCl_2(NH_3)L]$. The synthesis of $[PtCl_2(NH_3)L]$ is performed at about 30–60° C. in ammonium hydroxide solution. It is more preferred to perform the reaction at about 35–55° C., while about 40–50° C. is most preferred reaction temperature. In general, a higher reaction temperature shortens the reaction time but could also promote the formation of Pt multi ammine/amine side products. The greater formation of side products decreases the yield of the reaction.

The reaction is performed at about pH 7–14. A pH of about 7–12 is more preferred, while a pH of 8–10 is the most preferred. Performing the reaction at about pH> to 10 can again result in lower yields due to the increased formation of Pt multi amine side products.

The reaction is performed at a concentration of 1 g of $K[PtCl_3L]$ per 3–10 mL of solvent. A concentration of 1 g of $K[PtCl_3L]$ per 4–8 mL of solvent is more preferable, while a concentration of 1 g of $K[PtCl_3L]$ per 5–7 mL of solvent is most preferred. It was unexpected that performing the reaction at a high concentration would efficiently generate the product at a high yield. The reaction can be performed at a much more dilute concentration but the yield of the reaction was low due to the formation of side products. Larger volumes of solvents and more dilute concentration also requires the disposal of larger volumes of ecologically harmful solvents and waste. It is preferred to perform this reaction in strictly aqueous solutions. However, combination of organic and aqueous solvents can also be used. Specifically, the present method provides that the second reacting step 1b) is performed at a solvent to platinum ratio of less than or equal to about 5:1 (ml solvent)/(mmole platinum.). The second step of the process is performed with a $NH_3$/Pt ratio range of about 3 to 7. A $NH_3$/Pt ratio or about 4 to 6 is preferred, while a $NH_3$/Pt ratio of about 4.5 to 5.5 is most preferred. The present method provides that the second reacting step 1b) is performed at a molar ratio of free base form of L' to platinum between about 3:1 and 1:1. Large excess $NH_3$ decreases the time of reaction but may also increase the formation of Pt multi ammine/amine side products.

From cis-$[PtA_2(NH_3)(L)]$, c,t,c-$[PtA_2(OH)_2(NH_3)(L)]$ can be prepared by reacting a suspension of cis-$[PtA_2(NH_3)(L)]$ with hydrogen peroxide. Other Pt(IV) complexes of the formula c,t,c-$[PtA_2Y_2(NH_3)(L)]$ using methods known in the art, where Y is a halogen, hydroxy, carboxylate, carbamate or carbonate ester, other than where both Y are hydroxide, can be prepared from c,t,c-$[PtA_2(OH)_2(NH_3)(L)]$.

The examples used to illustrate the preparation of cis-$[PtCl_2(NH_3)(L)]$ and c,t,c-$[PtCl_2(OH)_2(NH_3)(L)]$ can also be used to prepare compounds of the general formula of cis-$[PtA_2(L)(L')]$ and c,t,c-$[PtA_2Y_2(L)(L')]$, where L and L' may be the same or different, provided that L' may be $NH_3$, but L may not be $NH_3$; and L and L' are each an amine or substituted amine that coordinates to the Pt atom through a nitrogen atom and is a heterocyclic amine or heteroaromatic amine or is represented by NRR'R", wherein R, R', or R" are independently selected from the group consisting of: hydrogen, substituted or unsubstituted straight, branched or cyclic aliphatic, aryl, nonaromatic or aromatic heterocyclic groups and preferably L is a substituted amine wherein the substituent sterically hinders access of the Pt atom to a DNA strand of cell, preferably a tumor cell. A may be the same or different and may be a halogen or a leaving group such as hydroxy, alkoxide, carboxylate or form a bi-dentate carboxylate, phosphoncarboxylate, diphosphonate or sulfate; and Y is a halogen, hydroxy, carboxylate, carbamate or carbonate ester.

For complexes Ia or Ib, methods are known in the art for converting Ligand A to different leaving group(s) such as halide, hydroxy, alkoxide, or mono-dentate carboxylate, or bi-dentate carboxylate, or bi-dentate phosphonocarboxylate, or bi-dentate phosphonate, or bi-dentate sulphate. Examples of such transformations are depicted in Equation 1 and Equation 2. Many other permutations and combinations of the leaving group conversions can be conceived that would lead to useful complexes. The method of preparation of the disclosed intermediates would be useful for the preparation of all these compounds.

Equation 1. Method of Preparing a Complex of Formula Ia Where the two Leaving Groups A are Halides and are Different.

Ia

Equation 2. Conversion of both ligands A (where A=halide to form a new compound where both A is the same and form a bi-dentate carboxylate.

Having now generally described the invention, the same will be more readily understood through reference to the following examples which are provided by way of illustration, and are not intended to be limiting of the present invention, unless specified.

BRIEF DESCRIPTION OF THE DRAWINGS

FIG. 4. Illustrates infrared and nuclear magnetic resonances spectrometric data for $[PtCl_2(NH_3)(2\text{-picoline})]$ prepared from the method disclosed in this invention.

EXAMPLES

In the examples illustrated below, the compounds were analyzed by $^1H$ and $^{195}Pt$ NMR spectroscopy, elemental analysis and by HPLC. NMR spectra were recorded on a Bruker Avance 300 ($^1H$ and $^{195}Pt$ NMR) spectrometer in DMF-$d^7$ and compared to the spectra of reference compounds synthesized using methods known in the art. Elemental Analysis (%C, %H, %N) were performed using a Perkin Elmer 2400 or Carlo Erba 1108 analyzer. The %Cl content was determined by silver nitrate titrations. Two HPLC methods (anionic and cationic HPLC methods) were used to analyze the compounds illustrated in the examples below. For the anionic HPLC method, the retention times of $K[PtCl_3(2\text{-picoline})]$ and $[PtCl_2(NH_3)(2\text{-picoline})]$ are 21.9 minutes and 4.2 minutes, respectively. For the cationic method, the retention times of [PtCl$_2$(NH$_3$)(2-picoline)] is 3 minutes. The HPLC retention times of the synthesized compounds were compared to the retention times of reference compounds prepared via method known in the art. The operating conditions of the anion and cation HPLC methods are as follows:

Cationic HPLC Method:

| Column: | Hichrom-RPB, 5 μm, 100 mm × 4.6 mm, 100 Å, ser # HIRPB3374 |
|---|---|
| Mobile Phase: | A: 0.02M H$_3$PO$_4$ (99.999%, Aldrich 34524-5), 5 mM Hexane Sulfonic Acid (Sigma 39705-9), adjusted to pH 2.7 with concentrated NaOH<br>B: Methanol (Fisher HPLC grade) |
| Gradient: | 0 min    95% A    5% B<br>6 min    95% A    5% B<br>20 min   50% A    50% B<br>25 min   50% A    50% B<br>25.01 min 95% A   5% B |
| Total Run Time: | 35.01 min |
| Flow rate: | 1.0 ml/min |
| Temperature: | 25° C. |
| Detector: | DAD @ 267 nm |
| Injection: | 10 μl |

Anionic HPLC Method:

| Column: | Hichrom-RPB C$_8$/C$_{18}$, 5 μm, 100 mm × 4.6 mm, 100 Å, ser # HIRPB3265 |
|---|---|
| Mobile Phase: | A: 0.02M H$_3$PO$_4$ (99.999%, Aldrich 45228-9), 5 mM tetrabutylammonium hydrogen sulfate (Sigma 39683-4), adjusted to pH 2.5 with concentrated NaOH<br>B: Methanol (Fisher HPLC grade) |
| Gradient: | 0 min    95% A    5% B<br>5 min    95% A    5% B<br>22 min   65% A    35% B<br>23 min   50% A    50% B<br>28 min   50% A    50% B<br>30 min   95% A    5% B |
| Total Run Time: | 40 min |
| Flow rate: | 1.0 ml/min |
| Temperature: | 35° C. |
| Detector: | DAD @ 230 nm |
| Injection: | 15 μl |

Examples 1–9 Exemplify Step one of the Process.

Example 1

Synthesis of K[PtCl$_3$(2-Picoline)] in N-methylpyrrolidinone

K$_2$[PtCl$_4$] was ground into a very fine powder with a mortar and pestle. 3.5047 g (8.443 mmoles) of K$_2$[PtCl$_4$] was placed in a 25 mL round bottom flask and 6–7 mL of dry NMP was added. 0.8648 g (9.286 mmoles) of 2-picoline was placed in 3–4 mL of NMP and divided in 5 equal portions. The first portion of 2-picoline was added to the Pt mixture. The mixture was completely immersed in a 60° C. oil bath and stirred at 1200 rpm. Subsequent portions of 2-picoline was added at 30–35 minutes intervals. The rate of 2-picoline addition was 20% every 30–35 minutes. After the addition of the last portion, the reaction was allowed to proceed for another 50 to 60 minutes. The reaction solution was orange in color at the end of the reaction. The reaction solution was allowed to cool to ambient temperature. 100 mL of methylene chloride was added to the reaction at ambient temperature. The addition of methylene chloride caused the precipitation of K[PtCl$_3$(2-picoline)] and KCl. The precipitate was collected by vacuum filtration using a glass frit and washed with methylene chloride (3×5 mL), followed diethyl ether (3×5 mL). The precipitate was dried under vacuum at ambient temperature for 16–24 hours and weighed. Yield: 3.8440 g (86.8%). Anal. Calcd (found) for C$_6$H$_7$N$_1$Cl$_3$KPt.1.2K$_1$Cl$_1$: C, 13.74 (13.54); H, 1.35 (1.39); N, 2.67 (2.59); Cl, 28.51 (28.32). $^1$H NMR (300 MHz, DMF-d$^6$): 9.12 (d, 1 pyridine H); 7.90 (t, 1 pyridine H); 7.61 (d, 1 pyridine H); 7.40 (t, 1 pyridine H); 3.40 (s, 3 methyl H). $^{195}$Pt NMR (300 MHz, DMF d$^6$): conforms to the $^{195}$Pt NMR spectrum of K[PtCl$_3$(2-picoline)] prepared via method known in the art. HPLC (anionic HPLC method): retention time conforms to retention time for reference compound.

Example 2

Synthesis of K[PtCl$_3$(2,6-Lutidine)] in N-methylpyrrolidinone

K$_2$[PtCl$_4$] was ground into a very fine powder with a mortar and pestle. 1.9427 g (4.68 mmoles) of K$_2$[PtCl$_4$] was placed in a 15 mL round bottom flask and 4 mL of dry NMP was added. 0.5501 g (5.13 mmoles) of 2,6-lutidine was placed in 3–4 mL of NMP and divided in 5 equal portions. The first portion of 2-picoline was added to the Pt mixture. The mixture was completely immersed in a 60° C. oil bath and stirred at 1200 rpm. Subsequent portions of 2-picoline was added at 30–35 minutes intervals. The rate of 2-picoline addition was 20% every 30–35 minutes. The total reaction time was 24 hours. The reaction solution was orange in color at the end of the reaction. The reaction solution was allowed to cool to ambient temperature. 200 mL of methylene chloride was added to the reaction at ambient temperature. The addition of methylene chloride caused the precipitation of K[PtCl$_3$(2-picoline)] and KCl. The precipitate was collected by vacuum filtration using a glass frit and washed with methylene chloride (3×5 mL), followed diethyl ether (3×5 mL). The precipitate was dried under vacuum at ambient temperature for 16–24 hours and weighed. Yield: 2.1415 g (84.7%). Anal. Calcd (found) for C$_7$H$_9$N$_1$Cl$_3$KPt.1.24K$_1$Cl$_1$: C, 15.57 (15.40); H, 1.68 (1.72); N, 2.59 (2.60); Cl, 27.83 (27.70). $^1$H NMR (300 MHz, DMF-d$^6$): 7.6 (t, 1 pyridine H); 7.28 (d, 2 pyridine H); 3.51 (s, 3 methyl H); 3.43 (s, 3 methyl H).

Example 3

Synthesis of K[PtCl$_3$(2-Picoline)] in Dimethylformamide at 50° C.

K$_2$[PtCl$_4$] was ground into a very fine powder with a mortar and pestle. 2.6461 g (6.375 mmoles) of K$_2$[PtCl$_4$] was placed in a 25 mL round bottom flask and 6 mL of dry DMF was added. 0.6233 g (6.693 mmoles) of 2-picoline was added to the Pt solution. The reaction was immersed in a 50° C. oil bath and allowed to proceed for approximately 120 minutes. The reaction solution was orange in color at the end of the reaction. The reaction solution was allowed to cool to ambient temperature. 100 mL of chloroform was added to the reaction at ambient temperature. The addition of chloroform caused the precipitation of K[PtCl$_3$(2,6-lutidine)] and KCl. The precipitate was collected by vacuum filtration using a glass frit and washed with methylene chloride (3×5 mL), followed diethyl ether (3×5 mL). The precipitate was dried under vacuum at ambient temperature for 16–24 hours and weighed. No black precipitate was observed when the product was dissolved in aqueous solution. Yield: 2.8565 g (84%). Anal. Calcd (found) for C$_6$H$_7$N$_1$Cl$_3$KPt.1.3K$_1$Cl$_1$: C, 13.58 (13.65); H, 1.33 (1.31); N, 2.67(2.64); Cl, 28.73 (28.78). $^1$H NMR (300 MHz, DMF-d$^6$): 9.12 (d, 1 pyridine H); 7.90 (t, 1 pyridine H); 7.61 (d, 1 pyridine H); 7.40 (t, 1 pyridine H); 3.40 (s, 3 methyl H). $^{195}$Pt NMR (300 MHz, DMF-d$^6$): conforms to the $^{195}$Pt NMR spectrum of K[PtCl$_3$ (2-picoline)] prepared via method known in the art. HPLC (anionic HPLC method): retention time conforms to retention time for reference compound.

Example 4

Synthesis of K[PtCl$_3$(2,6-Lutidine)] in Dimethylformamide at 50° C.

K$_2$[PtCl$_4$] was ground into a very fine powder with a mortar and pestle. 1.0900 g (2.62 mmoles) of K$_2$[PtCl$_4$] was placed in a 15 mL round bottom flask and 2–3 mL of dry DMF was added. 0.3078 g (2.87 mmoles) of 2,6-lutidine was placed in 1–2 mL of DMF and divided in 5 equal portions. The first portion of 2-picoline was added to the Pt mixture. The mixture was completely immersed in a 50° C. oil bath and stirred at 1200 rpm. Subsequent portions of 2-picoline was added at 30–35 minutes intervals. The rate of 2-picoline addition was 20% every 30–35 minutes. The total reaction time was 72 hours. The reaction solution was orange in color at the end of the reaction. The reaction solution was allowed to cool to ambient temperature and filtered. 100 mL of methylene chloride was added to the reaction at ambient temperature. The addition of methylene chloride caused the precipitation of K[PtCl$_3$(2,6-lutidine)]. The precipitate was collected by vacuum filtration using a glass frit and washed with methylene chloride (3×5 mL), followed diethyl ether (3×5 mL). The precipitate was dried under vacuum at ambient temperature for 16–24 hours and weighed. No black precipitate was observed when the product was dissolved in aqueous solution. Yield: 0.6815 g (53.1%). Anal. Calcd (found) for C$_7$H$_9$N$_1$Cl$_3$KPt.0.1K$_2$ [PtCl$_4$]: C, 17.19 (17.20); H, 1.85 (1.90); N, 2.86 (2.935); Cl, 24.64 (24.61). $^1$H NMR (300 MHz, DMF-d$^6$): 7.6 (t, 1 pyridine H); 7.28 (d, 2 pyridine H); 3.51 (s, 3 methyl H); 3.43 (s, 3 methyl H).

Example 5

Synthesis of [PtCl$_3$(2-Picoline)] in Acetone, Dichloromethane or Chloroform 1.0040 g (2.419 mmoles) K$_2$[PtCl$_4$] was placed in a 25 mL round bottom flask and 1 mL of acetone was added. 0.67 g (2.4 mmoles) of tetrabutylammonium chloride was dissolved in 2 mL of acetone and added to the K$_2$[PtCl$_4$] solution. 0.2783 g (2.988 mmoles) of 2-picoline was dissolved in 2 mL of acetone and added to the Pt solution. The reaction was heated at 60° C. The K$_2$[PtCl$_4$] gradually dissolved over a hour as it was converted to the more soluble tetrabutylammonium salt of [PtCl$_4$]$^{2-}$. The reaction solution was stirred at 50° C. for 16 hours. The reaction solution was filtered to remove KCl and the acetone removed under reduced pressure to yield an oil orange in color, corresponding to the [PtCl$_3$(2-picoline)]$^{1-}$ product. $^1$H NMR (300 MHz, DMF-d$^6$): 9.0 (d, 1 pyridine H); 7.8 (t, 1 pyridine H); 7.45 (d, 1 pyridine H); 7.25 (t, 1 pyridine H); 3.20 (s, 3 methyl H). $^{195}$Pt NMR (300 MHz, DMF-d$^6$): conforms to reference.

A identical procedure was used to prepare [PtCl$_3$(2-picoline)]$^{1-}$ with chloroform or Dichloromethane as the solvent. $^1$H NMR: conforms to reference.

To isolate [PtCl$_3$(2-picoline)$^{1-}$ as the potassium salt, the orange colored oil was dissolved in 2 mL of methanol. Potassium acetate dissolved in methanol was added, causing the precipitation of K[PtCl$_3$(2-picoline)]. The precipitate was dried under vacuum at ambient temperature for 16–24 hours and weighed. Yield: 0.5762 g (55%).

Example 6

Synthesis of [PtCl$_3$(Tributylamine)]$^-$ from Tetrabutylammonium Tetrachloroplatinate in Acetone 0.2715 g (0.33 mmoles) of tetrabutylammonium tetrachloroplatinate was dissolved in acetone. 0.1323 g (0.7135 mmoles) of tributylamine was added to the Pt solution. The reaction solution was heated at 60° C. overnight. The reaction solution was filtered to remove KCl and the acetone removed under reduced pressure to yield a orange oil, corresponding to the [PtCl$_3$(tributylamine)] product. $^{195}$Pt NMR (300 MHz, DMF-d$^6$): conforms to reference. To isolate [PtCl$_3$(tributylamine)]$^{2-}$ as the potassium salt, the orange colored oil was dissolved in 2 mL of methanol. Potassium acetate dissolved in methanol was added, causing the precipitation of K[PtCl$_3$(tributylamine)]. The precipitate was dried under vacuum at ambient temperature for 16–24 hours and weighed. Yield: 0.1577 g (64%)

Example 7

Synthesis of K[PtCl$_3$(2,5-Dimethylpyrazine)] in N-methylpyrrolidinone (NMP)

K$_2$PtCl$_4$ was ground to a very fine powder with a mortar and pestle. 1.0724 g (2.58 mmoles) of K$_2$PtCl$_4$ was charged to a 10 mL round bottom flask and ~5 mL of NMP added. The reaction vessel was stirred at ~700 rpm and immersed in an oil bath at 65° C. 0.3196 g (2.96 mmoles) of 2,5-dimethylpyrazine was mixed with ~1 mL of NMP. Approximately four equal portions of the 2,5-dimethylpyrazine solution were added to the reaction mixture in 30 minute intervals. After the last addition, the reaction was allowed to proceed for 60 minutes and was then cooled to ambient temperature. 150 mL of methylene chloride was added to the reaction mixture. The addition of methylene chloride caused the precipitation of the product. The precipitate was collected by vacuum filtration using a glass frit and was washed with methylene chloride (3×30 mL) and diethyl ether (3×10 mL). The precipitate was dried under vacuum at ambient temperature for 16 hours and weighed. Yield: 1.0507 g (66.3%). Anal. Calcd (found) for C$_6$H$_8$N$_2$Cl$_3$KPt.2.2KCl: C, 11.73 (11.50); H, 1.31 (1.50); N, 4.56 (4.27); Cl, 30.14 (29.86). $^1$H NMR (300 MHz, DMF-d$^7$) 9.11 (s, 1 pyrazine H); 8.68 (s, 1 pyrazine H); 3.31 (s, 3 methyl H), 2.68 (s, 3 methyl H).

Example 8

Synthesis of K[PtCl$_3$(4,6-Dimethylpyrimidine)] in NMP

K$_2$PtCl$_4$ was ground to a very fine powder with a mortar and pestle. 0.5277 g (1.27 mmoles) of K$_2$PtCl$_4$ was charged to a 15 mL round bottom flask and ~3 mL of NMP added. The reaction vessel was stirred vigorously and immersed in an oil bath at 65° C. 0.1549 g (1.43 mmoles) of 4,6-dimethylpyrimidine was mixed with ~1 mL of NMP. The 4,6-dimethylpyrimidine solution was added to the reaction mixture in approximately four equal portions over 30-minute intervals. After the last addition, the reaction was allowed to proceed for 60 minutes; it was then cooled to ambient temperature. The reaction mixture was quenched with ~80 mL of methylene chloride, which caused solids to precipitate. The precipitate was collected by vacuum filtration using a glass frit and washed with methylene chloride (3×30 mL) and diethyl ether (3×10 mL). The precipitate was dried under vacuum at ambient temperature for 16 hours and weighed. Yield: 0.4353 g (76.3%). $^1$H NMR (300 MHz, DMF-d$^7$) 9.58 (s, 1 pyrimidine H); 7.65 (s, 1 pyrimidine H); 3.32 (s, 3 methyl H), 2.65 (s, 3 methyl H).

Example 9

Synthesis of [PtCl$_3$(Diisopropylamine)]$^-$ from Tetrabutylammonium Tetrachloroplatinate in Acetone 0.7961 g (0.9687 mmoles) of tetrabutylammonium tetrachlorplatinate was placed in a 25 mL round bottom flask and 8 mL of acetone was added. 0.1699 g (1.679 mmoles) of diisopropylamine was dissolved in 2 mL of acetone and added to the Pt solution. The reaction was immersed in an oil bath at 60° C. and stirred for 60 hours. The red [PtCl$_4$]$^-$ was converted to the orange [PtCl$_3$(diisopropylamine)]$^-$ as confirmed by $^{195}$Pt NMR spectroscopy. The [PtCl$_3$(diisopropylamine)]$^-$ could be used to prepare [PtCl$_2$(NH$_3$)(diisopropylamine)] directly without isolation as the potassium or tetrabutylammonium salt. $^{195}$Pt NMR (300 MHz, DMF-d$^7$): conforms to the $^{195}$Pt NMR spectrum of [PtCl$_3$(diisopropylamine)]$^-$ prepared via method known in the art.

Examples 10–18 Exemplify Step 2 of the Process

Example 10

Synthesis of [PtCl$_2$(NH$_3$)(2-Picoline)] in Aqueous Solution 6.819 g (12.50 mmoles) of K[PtCl$_3$(2-picoline)].1.5 KCl was placed in a 25 mL round bottom flask and 10 mL of 2.5 N KCl solution added. 8.2688 g (63.12 mmoles) of ammonium acetate trihydrate was dissolved in 25 mL of 2.5 N ammonium hydroxide solution and added to the stirring Pt mixture. The total volume of the reaction was ~35 mL. The orange colored mixture was immersed in a 45° C. oil bath and was stirred for 1 hour in the dark at >1000 rpm. The orange mixture gradually turned into a yellow colored mixture. The yellow precipitate was collected by vacuum filtration using a glass frit and washed with water (2×5 mL) and acetone (3×5 mL). The precipitate was dried under vacuum at ambient temperature for 16–24 hours and weighed. Yield: 3.8996 g (83%). Anal. Calcd (found) for C$_6$H$_{10}$N$_2$Cl$_2$Pt: C, 19.16 (19.25); H, 2.68 (2.72); N, 7.45 (7.43); Cl, 18.85 (18.81). $^1$H NMR (300 MHz, DMF-d$^6$): 9.19 (d, 1 pyridine H); 8.03 (t, 1 pyridine H); 7.15 (d, 1 pyridine H); 7.51 (t, 1 pyridine H); 4.39 (bs, 3 NH$_3$H); 3.34 (s, 3 methyl H). $^{195}$Pt NMR (300 MHz, DMF-d$^6$): conforms to the $^{195}$Pt NMR spectrum of [PtCl$_2$(NH$_3$)(2-picoline)] prepared via method known in the art. HPLC(cationic HPLC method): retention time conforms to retention time for reference compound.

Example 11

Synthesis of [PtCl$_2$(NH$_3$)(2,6-Lutidine)] in Aqueous Solution 1.7412 g (3.224 mmoles) of K[PtCl$_3$(2,6-lutidine)].1.24 KCl was placed in a 25 mL round bottom flask and 3 mL of 2.5 N KCl solution added. 1.3478 g (17.48 mmoles) of ammonium acetate was dissolved in 6.4 mL of 2.5 N ammonium hydroxide solution and added to the stirring Pt mixture. The total volume of the reaction was ~9.5 mL. The orange colored mixture was immersed in a 45° C. oil bath and was stirred for 40 hour in the dark at >1000 rpm. The orange mixture gradually turned into a yellow colored mixture. The yellow precipitate was collected by vacuum filtration using a glass frit and washed with water (2×5 mL) and acetone (3×5 mL). The precipitate was dried under vacuum at ambient temperature for 16–24 hours and weighed. Yield: 0.9791 g (78%). $^1$H NMR (300 MHz, DMF-d$^6$): 7.87 (t, 1 lutidine H); 7.49 (d, 2 lutidine H); 4.28 (bs, 3 NH$_3$H); 3.49 (s, 6 methyl H). $^{195}$Pt NMR (300 MHz, DMF-d$^6$): conforms to reference. Analysis Calculated (found) for C$_7$H$_{12}$N$_2$Cl$_2$Pt: C, 21.55 (21.70); H, 3.10 (3.13); N, 7.18 (7.07); Cl, 18.17 (18.28).

Example 12

Synthesis of [PtCl$_2$(NH$_3$)(2,5-Dimethylpyrazine)] in Aqueous Solution 0.5325 g (0.8665 mmoles) of K[PtCl$_3$(2,5-dimethylpyrazine)].2.2 KCl was charged to a 15 mL round bottom flask and 1.0 mL of 2.5 M KCl solution added. 0.335 g (4.35 mmoles) of ammonium acetate was dissolved in 1.75 mL of 2.5 M (4.38 mmoles) ammonium hydroxide solution and added to the stirring reaction mixture. The reaction mixture was immersed in a 45° C. oil bath. After 15 minutes, the mixture became yellow in colour. After 1 hour, the mixture was cooled to ambient temperature and the yellow precipitate collected by vacuum filtration using a glass frit. The precipitate was washed with water (2×10 mL) and acetone (1×10 mL) and dried under vacuum at ambient temperature. $^1$H NMR (300 MHz, DMF-d$^7$): 9.16 (s, 1 pyrazine H); 8.80 (s, 1 pyrazine H); 4.70 (bs, 3 NH$_3$H), 3.26 (s, 3 methyl H); 2.69 (2,3 methyl H).

Example 13

Synthesis of [PtCl$_2$(NH$_3$)(2-Picoline)] in N-Methylpyrrolidinone/Aqueous Solution 1.84 g (14.0 mmoles) of ammonium acetate trihydrate was dissolved in 4.63 mL of 2.9 N ammonium hydroxide. The aqueous solution was added to 2.68 mmoles of [PtCl$_3$(2-picoline)]$^-$ in 2.5 mL of N-methylpyrrolidinone. The reaction solution was stirred at 45° C. for 80 minutes. Yellow precipitate formed. The precipitate was collected by vacuum filtration using a glass frit and washed with water (2×5 mL) and acetone (3×5 mL). The precipitate was dried under vacuum at ambient temperature for 16–24 hours and weighed. Yield: 0.3391 g (34%). Anal. Calcd (found) for C$_6$H$_{10}$N$_2$Cl$_2$Pt: C, 19.16 (19.22); H, 2.68 (2.69); N, 7.45 (7.23); Cl, 18.85 (18.83). $^1$H NMR (300 MHz, DMF-d$^6$): 9.2 (d, 1 pyridine H); 8.0 (t, 1 pyridine H); 7.2 (d, 1 pyridine H); 7.5 (t, 1 pyridine H); 3.4 (s, 3 methyl H). $^{195}$Pt NMR (300 MHz, DMF-d$^6$): conforms to the $^{195}$Pt NMR spectrum of [PtCl$_2$(NH$_3$)(2-picoline)] prepared via method known in the art. HPLC(cationic HPLC method): retention time conforms to retention time for reference compound.

Example 14

Synthesis of [PtCl$_2$(NH$_3$)(2-Picoline)] in Dimethylformamide/Aqueous Solution

[PtCl$_2$(NH$_3$)(2-picoline)] was prepared in dimethylformamide/aqueous solution as described in Example 13). Anal. Calcd (found) for C$_6$H$_{10}$N$_2$Cl$_2$Pt: C, 19.16 (19.30); H, 2.68 (2.62); N, 7.45 (7.18); Cl, 18.85 (18.59). $^1$H NMR (300 MHz, DMF-d$^6$): 9.1 (d, 1 pyridine H); 8.1 (t, 1 pyridine H); 7.3 (d, 1 pyridine H); 7.4 (t, 1 pyridine H); 3.4 (s, 3 methyl H). $^{195}$Pt NMR (300 MHz, DMF-d$^6$): conforms to the $^{195}$Pt NMR spectrum of [PtCl$_2$(NH$_3$)(2-picoline)] prepared via method known in the art.

Example 15

Synthesis of [PtCl$_2$(NH$_3$)(Diisopropylamine)] in Acetone/Aqueous Solution 6 ml 2.5 N ammonium hydroxide was added to [PtCl$_3$(NH$_3$)(diisopropylamine)]$^-$ (~2.69 mmoles) in 2.5 ml acetone. The pH of the solution was 12. The reaction solution was stirred at 45° C. for 48 hours. Yellow precipitate formed. the precipitate was collected by vacuum filtration using a glass frit and washed with water (2×5 mL) and diethyl ether (3×5 mL). The precipitate was dried under vacuum at ambient temperature for 16–24 hours. Anal. Calcd (found) for C$_6$H$_{18}$N$_2$Cl$_2$Pt.0.095C$_6$H$_{30}$N$_2$Cl$_2$Pt: C, 20.00 (19.98); H, 4.90 (4.89); N, 7.16 (7.12); Cl, 18.11 (17.93). $^1$H NMR (300 MHz, DMF-d$^7$): 4.5 (bs, 1 diisopropylamine H), 3.9 (bs, 3 NH$_3$H); 3.3 (m, 2 methine H in diisopropylamine); 1.7 (d, 6 methyl H in diisopropylamine); 1.5 (d, 6 methyl H in diisopropylamine). $^{195}$Pt NMR (300 MHz, DMF-d$^6$): conforms to the $^{195}$Pt NMR spectrum of [PtCl$_2$(NH$_3$)(diisopropylamine)] prepared via method known in the art.

Example 16

Synthesis of [PtCl$_2$(2-Picoline)(NH$_2$CH$_3$)] in Aqueous Solution 0.5055 g (1.17 mmoles) of K[PtCl$_3$(2-picoline)] was placed in a 15 mL round bottom flask and 1 mL of 2.5 M KCl solution added. The suspension was immersed in a 45° C. oil bath and stirred at ~1000 rpm. After five minutes, a solution consisting of 0.1704 g of 40% methylamine (2.19 mmoles) and 1 mL water was added to the reaction mixture. The pH of the solution was 12. Heating was discontinued after a total reaction time of 1 hour. The reaction mixture was then cooled to ambient temperature. A pale yellow precipitate was collected by vacuum filtration using a glass frit and washed with water (2×20 mL) and acetone (3×20 mL). The precipitate was dried under vacuum at ambient temperature for 16 hours. Anal. Calcd (found) for C$_7$H$_{12}$N$_2$Cl$_2$Pt: C, 21.55 (21.73); H, 3.10 (3.09); N, 7.18 (7.14); Cl, 18.17 (18.20). $^1$H NMR (300 MHz, DMF-d$^7$): 9.24 (d, 1 pyridine H), 8.06 (t, 1 pyridine H); 7.75 (d, 1 pyridine H); 7.55 (t, 1 pyridine H); 5.22 (bs, 2 methylamine H); 3.35 (s, 3 methyl H of 2-picoline); 2.45 (t, 3 methyl H of methylamine).

Example 17

Synthesis of [PtCl$_2$(2-Picoline)(NH(CH$_3$)$_2$)] in Aqueous Solution 0.5459 g (1.26 mmoles) of K[PtCl$_3$(2-picoline)] was placed in a 15 mL round bottom flask and 1.5 mL of 2.5 M KCl solution added. The suspension was immersed in a 45° C. oil bath and stirred vigorously. After five minutes, a solution consisting of 0.1426 g of 40% dimethylamine (1.27 mmoles) and ~1 mL of water was added to the reaction mixture. The pH of the solution was 12. After one hour of reaction the heating was discontinued and the reaction mixture was cooled to ambient temperature. A yellow precipitate was collected by vacuum filtration using a glass frit and washed with water (2×20 mL) and acetone (2×10 mL). The precipitate was dried under vacuum at ambient temperature for 16 hours. Anal. Calcd (found) for C$_8$H$_{14}$N$_2$Cl$_2$Pt: C, 23.77 (24.00); H, 3.48 (3.49); N, 6.93 (6.80); Cl, 17.54 (17.63). $^1$H NMR (300 MHz, DMF-d$^7$): 9.31 (d, 1 pyridine H), 8.09 (t, 1 pyridine H); 7.78 (d, 1 pyridine H); 7.58 (t, 1 pyridine H); 6.06 (bs, 1 NH H); 3.37 (s, 3 methyl H of picoline); 2.76 (d, 3 methyl H of dimethylamine); 2.70 (d, 3 methyl H of dimethylamine).

Example 18

Synthesis of [PtCl$_2$(2-Picoline)(NBu$_3$)] in Aqueous Solution 0.6289 g (1.45 mmoles) of K[PtCl$_3$(2-picoline)] was placed in a 15 mL round bottom flask and 1.0 mL of 2.5 M KCl solution added. The reaction mixture was immersed in a 45° C. oil bath and stirred vigorously for 5 minutes. 0.2735 g (1.47 mmoles) of tributylamine was dissolved in 1.0 mL of water and added to the orange reaction mixture. The pH of the solution was 12. After one hour heating was discontinued. After cooling to ambient temperature, the precipitate was collected by vacuum filtration using a glass frit. The solids collected were dried under vacuum at ambient temperature. $^1$H NMR (300 MHz, DMF-d$^7$): 9.14 (d, 1 pyridine H), 7.90 (t, 1 pyridine H); 7.60 (d, 1 pyridine H); 7.42 (t, 1 pyridine H); 3.41 (s, 3 methyl H of 2-picoline); 3.28 (d, 2 methylene H of tributylamine); 1.88 (tt, 2 methylene H of tributylamine); 1.56 (m, 2 methylene H of tributylamine); 1.10 (t, 3 methyl H of tributylamine).

Examples 19–23 Exemplify Additional Steps of the Process

Example 19

Synthesis of c,t,c-[PtCl$_2$(OH)$_2$(NH$_3$)(2-Picoline)]

5.0 mL of water and 5.0 mL 30% H$_2$O$_2$ was added to a suspension of 3.142 g of ZD0473 in 15–20 mL of heptane. This mixture was stirred and heated to ~80° C. for 2 hours. The mixture was cooled to room temperature and then stirred for 1 hour in an ice bath. The bright yellow solid was collected by vacuum filtration and washed with water and methanol. The product was dried under vacuum at ambient temperature overnight. Yield: 2.975 g (87%). Anal. Calcd (found) for C$_6$H$_{12}$N$_2$Cl$_2$O$_2$Pt: C, 17.57 (17.67); H, 2.95 (2.93); N, 6.83 (6.79); Cl, 17.29 (17.38).

Example 20

Synthesis of c,t,c-[PtCl$_2$(OH)$_2$(NH$_3$)(2,3-Dimethylpyrazine)]

2.5 mL of water and 3.5 mL 30% H$_2$O$_2$ was added to a suspension of 1.6731 g of cis-[PtCl$_2$(NH$_3$)(2,3-dimethylpyrazine)] in 10 mL of heptane. This mixture was stirred and heated to ~80° C. for 2 hours. The mixture was cooled to room temperature and then stirred for 1 hour in an ice bath. The bright yellow solid was cooled by vacuum filtration and washed with water and methanol. The product was dried under vacuum at ambient temperature overnight. Yield: 1.1341 g (62%). Anal. Calcd (found) for C$_6$H$_{13}$N$_3$Cl$_2$O$_2$Pt: C, 16.95 (16.81); H, 3.08 (3.12); N, 9.88 (9.66); Cl, 16.68 (16.44).

Example 21

Synthesis of PtCl(OH)$_3$(NH$_3$)(2-Picoline)]

0.246 g of LiOH.H2O was dissolved in 5 mL of water. 2.402 g of c,t,c-[PtCl$_2$(OH)$_2$(NH$_3$)(2-picoline)] was suspended in this solution. The mixture was stirred overnight at ambient temperature. The yellow solid gradually dissolved overnight. The pH of the solution was adjusted to 7. The solvent was removed under reduced pressure to yield a yellow solid. In order to wash away the resulting LiCl, the solid was stirred in 10 mL of ethanol for 30 min. The mixture was centrifuged and the supernatant decanted off. This washing process was repeated until lithium chloride was removed. The product was dried under vacuum at ambient temperature overnight. Yield: 1.209 (50%). Anal. Calcd (found) for $C_6H_{13}N_2ClO_3Pt \cdot 2H_2O \cdot 0.12LiCl$: C, 16.65 (16.45); H, 3.96 (4.04); N, 6.47 (6.75); Cl, 9.17 (9.47).

Example 22

Synthesis of PtCl(OAc)$_3$(NH$_3$)(2-Picoline)]

0.352 g of PtCl(OH)$_3$(NH$_3$)(2-picoline)] was added in small portions to 1.1 mL of acetic anhydride at 0° C. This mixture was stirred vigorously at ambient temperature. After 3 days, the solid dissolved into the solution. The solvent was removed under reduced pressure to yield a yellow solid. The product was dried under vacuum at ambient temperature overnight. Yield: 0.314 g (70%). Anal. Calcd (found) for $C_{12}H_{19}N_2ClO_6Pt$: C, 27.83 (27.93); H, 3.70 (3.66); N, 5.41 (5.34); Cl, 6.85 (7.00).

Example 23

Synthesis of PtCl$_2$(OAc)$_2$(NH$_3$)(2-Picoline)]

1.367 g of c,t,c-[PtCl$_2$(OH)$_2$(NH$_3$)(2-picoline)] was added in small portions to 3.1 mL of acetic anhydride at 0° C. This mixture was stirred vigorously at room temperature. After 4 days, the solid was collected by vacuum filtration and washed with diethyl ether. The product was dried under vacuum at ambient temperature overnight. Yield: 1.318 g (96%). Anal. Calcd (found) for $C_{10}H_{16}N_2Cl_2O_4Pt$: C, 24.30 (24.32); H, 3.26 (3.15); N, 5.67 (5.66); Cl, 14.35 (14.29).

TABLE 1

Summary of the Examples of Step 1 of the process to form an intermediate [PtA$_3$(L)]$^{1-}$ of formula Ia.

| Example | L | A | solvent | Temp | pH |
|---|---|---|---|---|---|
| Example 1) | 2-picoline | Cl | N-methyl-pyrrolidinone | 60° C. | NA |
| Example 2) | 2-picoline | Cl | N-methyl-pyrrolidinone | 60° C. | NA |
| Example 3) | 2-picoline | Cl | dimethylformamide | 50° C. | NA |
| Example 4) | 2,6-lutidine | Cl | dimethylformamide | 50° C. | NA |
| Example 5) | 2-picoline | Cl | acetone or chloroform or dichloromethane | 60° C. | NA |
| Example 6) | N(CH$_2$CH$_2$CH$_2$CH$_3$)$_3$ | Cl | acetone | 60° C. | NA |
| Example 7) | methylpyrazine | Cl | N-methyl-pyrrolidinone | 65° C. | NA |
| Example 8) | dimethylpyrimidine | Cl | N-methyl-pyrrolidinone | 65° C. | NA |
| Example 9) | diisopropyl-NH | Cl | acetone | 60° C. | NA |

TABLE 2

Summary of the Examples of Step 2 of the process to form an cisplatinum complex of the general formula Ia.

| Example | L | L' | A | solvent | Temp | pH |
|---|---|---|---|---|---|---|
| Example 10) | 2-picoline | NH$_3$ | Cl | aqueous | 45° C. | 9–10 |

TABLE 2-continued

Summary of the Examples of Step 2 of the process to form an cisplatinum complex of the general formula Ia.

| Example | L | L' | A | solvent | Temp | pH |
|---|---|---|---|---|---|---|
| Example 11) |  | $NH_3$ | Cl | aqueous | 45° C. | 9–10 |
| Example 12) |  | $NH_3$ | Cl | aqueous | 45° C. | 9–10 |
| Example 13) |  | $NH_3$ | Cl | N-methylpyrrolidinone-aqueous mixture | 45° C. | 9–10 |
| Example 14) |  | $NH_3$ | Cl | dimethylformamide-aqueous mixture | 45° C. | 9–10 |
| Example 15) |  | $NH_3$ | Cl | Acetone-aqueous mixture | 45° C. | 12 |
| Example 16) |  | $NH_2(CH_3)$ | Cl | aqueous | 45° C. | 12 |
| Example 17) |  | $NH(CH_3)_2$ | Cl | aqueous | 45° C. | 12 |
| Example 18) |  | $N(butyl)_3$ | Cl | aqueous | 45° C. | 12 |

TABLE 3

Summary of the examples of platinum complexes of the general formula Ib.

| Example | L | L' | A | Y |
|---|---|---|---|---|
| Example 19) |  | $NH_3$ | Cl | OH |
| Example 20) |  | $NH_3$ | Cl | OH |
| Example 21) |  | $NH_3$ | Cl/OH | OH |
| Example 22) |  | $NH_3$ | Cl/OAc | OAc |
| Example 23) |  | $NH_3$ | Cl | OAc |

This invention has been described by a direct description and by examples. As noted above, the examples are meant to be only examples and not to limit the invention in any meaningful way. Additionally, one having ordinary skill in the art to which this invention pertains in reviewing the specification and claims which follow would appreciate that there are equivalents to those claimed aspects of the invention. The inventors intend to encompass those equivalents within the reasonable scope of the claimed invention.

We claim:

1. A method to prepare a cisplatinum complex of the formula Ia or Ib comprising the steps of:
a) reacting [PtA$_4$]$^2$ or a salt thereof with L in a first aprotic solvent at a temperature of 30° C. to 100° C. to form [PtA$_3$(L)]$^-$, with the proviso that when the first solvent is DMF, the temperature is below 60° C.;
b) without evaporating the first solvent, reacting the [PtA$_3$(L)]$^-$ with L' in a second solvent to form cis-[PtA$_2$(L')(L)];
c) when the cisplatinum complex is of the formula Ib and Y is hydroxy or a halogen, reacting the cis-[PtA$_2$(L')(L)] formed in step b) with H$_2$O$_2$ when Y is hydroxy, or a halogen when Y is a halogen, to form c,t,c-[PtA$_2$Y$_2$(L')(L)]; and
d) when the cisplatinum complex is of the formula Ib and Y is carboxylate, carbamate or carbonate ester, first forming [PtA$_2$OH$_2$(L')(L)] from [PtA$_2$(L')(L)] by reacting the cis-[PtA$_2$(L')(L)] formed in step b) with H$_2$O$_2$, and then reacting the [PtA$_2$OH$_2$(L')(L)] with an acylating agent to form [PtA$_2$Y$_2$(L')(L)];
wherein L and L' are different and are each an amine or a substituted amine, wherein said substituted amine is substituted with at least one straight, branched or cyclic aliphatic, aryl, nonaromatic or aromatic heterocyclic group, with the proviso that only L' can be NH$_3$ and that at least one of L and L' is a substituted cyclic amine;
wherein A may be the same or different and is a halide or a leaving group; and
wherein Y is halogen, hydroxy, carboxylate, carbamate or carbonate ester.

2. A method to prepare a cisplatinum complex of the formula Ia' or Ib' comprising the steps of:
a) reacting [PtA$_4$] or a salt thereof with L in a first aprotic solvent at a temperature of 30° C. to 100° C. to form [PtA$_3$(L)]$^-$, with the proviso that when the first solvent is DMF, the temperature is below 60° C.;
b) without evaporating the first solvent, reacting [PtA$_3$(L)] with L' in a second solvent to form cis-[PtA$_2$(L')(L)];
c) when the cisplatinum complex is of the formula Ib' and Y is hydroxy or a halogen, reacting the cis-[PtA$_2$(L')(L)] formed in step b) with H$_2$O$_2$ when Y is hydroxy, or a halogen when Y is a halogen, to form c,t,c-[PtA$_2$Y$_2$(L')(L)];
d) when the cisplatinum complex is of the formula Ib' and Y is carboxylate, carbamate or carbonate ester, first forming [PtA$_2$OH$_2$(L')(L)] from [PtA$_2$(L')(L)] by reacting the cis-[PtA$_2$(L')(L)] formed in step b) with H$_2$O$_2$, and then reacting the [PtA$_2$OH$_2$(L')(L)] with an acylating agent to form [PtA$_2$Y$_2$(L')(L)]; and
e) converting A to A', wherein A' is a different halide or leaving group than A;
wherein L and L' are different and are each an amine or a substituted amine, wherein said substituted amine is substituted with at least one straight, branched or cyclic aliphatic, aryl, nonaromatic or aromatic heterocyclic group, with the proviso that only L' can be NH$_3$ and that at least one of L and L' is a substituted cyclic amine;
wherein A and A' may be the same or different and are a halide or a leaving group; and
wherein Y is halogen, hydroxy, carboxylate, carbamate or carbonate ester.

3. The method of claim 1, wherein in step a) the [PtA$_4$]$^{2-}$ is in the form of a finely ground platinum salt.

4. The method of claim 1, wherein said aprotic solvent is selected from the group consisting of: acetone, chloroform, dimethylacetamide, dimethylformamide, dichloromethane, N-methylpyrolidone and tetrahydrofuran.

5. The method of claim 1, wherein said aprotic solvent is N-methylpyrrolidone.

6. The method of claim 1, wherein in step a) the amine L is added in small portions during the course of said reacting step.

7. The method of claim 1, wherein step a) is performed at a temperature of between about 40–70° C.

8. The method of claim 7, wherein step a) is performed between about 50–65° C.

9. The method of claim 1, wherein step a) is performed at a solvent to platinum ratio of less than about 6:1 (ml solvent)/(mmole platinum).

10. The method of claim 9, wherein step a) is performed at a solvent to platinum ratio of less than about 2:1.0 (ml solvent)/(mmole platinum).

11. The method of claim 9, wherein in step a) the first solvent contains less than 10% water w/w.

12. The method of claim 1, wherein in step b) the second solvent is an aqueous solvent.

13. The method of claim 1, wherein in step b) the second solvent is a combination of an aqueous solvent and an organic solvent.

14. The method of claim 1, wherein in step b) the second solvent contains between about 0.1 and 6N chloride.

15. The method of claim 1, wherein step b) is performed at a temperature of between about 30–60° C.

16. The method of claim 15, wherein step b) is performed at a temperature of between about 40–50° C.

17. The method of claim 1, wherein step b) is performed at a pH between about 7 and 14.

18. The method of claim 17, wherein step b) is performed at a pH between about 7 and 12.

19. The method of claim 18, wherein step b) is performed at a pH between about 8 and 10.

20. The method of claim 1, wherein step b) is performed at a solvent to platinum ratio of less than or equal to about 5:1 (ml solvent)/(mmole platinum.).

21. The method of claim 1 wherein step b) is performed at a molar ratio of free base form of L' to platinum between 3:1 and 1:1.

22. The method of claim 2, wherein A' is a selected from the group consisting of chlorine, hydroxy, alkoxy, carboxylate, and bi-dentate carboxylate, phosphonocarboxylate, diphosphonate or sulfate.

23. The method of claim 22, wherein A is chloride.

24. The method of claim 1, wherein L is 2-picoline.

25. The method of claim 1, wherein at least one of L and L' is a heterocyclic amine or heteroaromatic amine or is represented by NRR'R", wherein R, R', or R" are independently selected from the group consisting of hydrogen, substituted or unsubstituted straight, branched or cyclic aliphatic, aryl, nonaromatic or aromatic heterocyclic groups.

26. The method of claim 25, wherein L' is NH₃.

27. The method of claim 26, wherein A is chloride.

28. The method of claim 1, wherein L is

L' is NH₃, A is Cl and Y is OH.

29. The method of claim 1, wherein L is

L' is NH₃, A is Cl and Y is OH.

30. The method of claim 1, wherein L is

L' is NH₃, A, A is Cl, OH, and Y is OH.

31. The method of claim 1, wherein L is

L' is NH₃, A, A is Cl, OAc and Y is OAc.

32. The method of claim 1, wherein L is

L' is NH₃, A is Cl, and Y is OAc.

33. A cisplatinum complex of the formula wherein L is

L' is NH₃, A, A is Cl, OH, and Y is OH.

* * * * *

UNITED STATES PATENT AND TRADEMARK OFFICE
CERTIFICATE OF CORRECTION

PATENT NO.     : 6,518,428 B1
DATED          : February 11, 2003
INVENTOR(S)    : Ernest S. Y. Wong et al.

It is certified that error appears in the above-identified patent and that said Letters Patent is hereby corrected as shown below:

<u>Title page,</u>
Item [75], Inventors, delete "Gianomenico" and insert -- Giandomenico --.

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,518,428 B1
DATED         : February 11, 2003
INVENTOR(S)   : Ernest S. Y. Wong et al.

It is certified that error appears in the above-identified patent and that said Letters Patent is hereby corrected as shown below:

Column 22,
Line 2, "[PtA$_3$(L)]" should be changed to: -- [PtA$_3$(L)]$^-$ --

Signed and Sealed this

Twenty-eighth Day of June, 2005

JON W. DUDAS
*Director of the United States Patent and Trademark Office*